United States Patent [19]
Schülken et al.

[11] Patent Number: 5,499,990
[45] Date of Patent: Mar. 19, 1996

[54] SUTURING INSTRUMENT

[75] Inventors: Heinrich Schülken, Stutensee; Roland Neeb, Waghäusel; Karl Schlipf, Karlsruhe; Bertram Kuntz, Steinfeld, all of Germany

[73] Assignee: Forschungszentrum Karlsruhe GmbH, Karlsruhe, Germany

[21] Appl. No.: 361,036

[22] Filed: Dec. 21, 1994

[30] Foreign Application Priority Data

May 23, 1992 [DE] Germany ............ 42 17 202.0

[51] Int. Cl.⁶ .................................................. A61B 17/00
[52] U.S. Cl. ........................... 606/144; 606/103; 606/139
[58] Field of Search ............................. 606/139, 144, 606/145–148, 151, 103, 142, 143, 170, 167, 205–208; 112/169, 80.03

[56] References Cited

U.S. PATENT DOCUMENTS

3,545,444  12/1970  Green ............................ 606/143
4,204,541  5/1980   Kapitanov ...................... 606/145
5,261,917  11/1993  Hasson et al. .................. 606/139
5,356,424  10/1994  Buzerak et al. ................ 112/80.03
5,417,700  5/1995   Egan ............................ 606/144

Primary Examiner—Stephen C. Pellegrino
Assistant Examiner—Jeffrey A. Schmidt
Attorney, Agent, or Firm—Klaus J. Bach

[57] ABSTRACT

In a suturing instrument for remote suturing of the edges of tissue wherein a stationary and a pivotal jaw are arranged at the distal end of an instrument shaft and a suturing wire guide channel extends through the instrument shaft for supplying a suturing wire from the instrument's proximal end to the stationary jaw and wherein an outer tube is movably disposed on the instrument shaft for engaging the pivotal jaw to move it toward and from the stationary jaw and hold the jaws in an operating position in which they are arranged parallel to one another, the jaws have spaced wire guide grooves with groove bases defining, in the operating position of the jaws, a screw line which is followed by the suturing wire when it is advanced by advancing means operated by a handle disposed at the proximal end of the suturing instrument.

11 Claims, 8 Drawing Sheets

SUTURING INSTRUMENT

The present application is a continuation-in-part application of International application PCT/DE93/00418 filed May 13, 1993, claiming the priority of German application P 42 17 202.0 filed May 23, 1992.

BACKGROUND OF THE INVENTION

The invention relates to a suturing instrument for remotely joining the edges of a wound within the body of a patient.

Such a surgical instrument is known, for example, from U.S. Pat. No. 4,935,027 (Yoon); it is suitable for conventional as well as minimal invasive (MIC) surgery. It comprises outer and inner tubes which are movable axially relative to one another and which carry at their distal ends (remote from the operator and to be inserted into the body of a patient) two pliers or forceps-like jaws or hooks which are hollow and are received within the suturing material. This U.S. patent shows an arrangement wherein both jaws or hooks are movable or One jaw is stationary and the other is movable. At the proximal end (the end next to the operator) there is a handle portion which is connected to the inner tube and to the outer tube for moving the jaws or hooks relative to one another. Within the inner tube there is the supply passage for the suturing material.

With this suturing instrument however, only single-knot sutures can be applied wherein each suture must be secured with a knot movable toward the tissue. The applying of the knots is complicated and time-consuming. Furthermore, the tissue is penetrated not only by the suturing material but also by the hook.

DE 31 41 647 A1 discloses a surgical instrument for the application of clamps. This instrument includes an elongated body with a handle portion at the proximal end. At the distal end of the elongated body there is a stationary support jaw with a recess for locking the clamp. Furthermore there is at the distal end of the elongated body a movable engagement jaw with the clamp applicator. The engagement jaw is mounted to the body so as to be movable back and forth in the direction of the stationary support jaw. The instrument also includes a drive mechanism for operating the engagement jaw and the clamp applicator. The movable engagement jaw includes a channel for feeding a wire thereto and is provided, at the channel exit, with a cutter which is movable back and forth in a plane normal to the channel for cutting off wire pieces and which is operatively connected to the drive mechanism.

However this instrument is relatively large and already because of its size and design is not suitable for minimally invasive surgery.

Another suturing instrument is known from EP 01 74 843 A2. This suturing instrument includes a block defining a one-sided open cavity receiving a suturing material support structure which can be operated by a handle portion at the proximal end of the elongated instrument. There is further a channel extending into the cavity which receives a needle with an eye through which the suturing material passes. The channel is arranged opposite the suturing material support structure. Furthermore a suction structure extends into the cavity. The block is placed onto the tissue to be sutured in such a way that the cavity is closed by the tissue. Then the cavity is evacuated by the suction structure such that the adjacent tissue enters the cavity. Then a suture is applied by means of the needle and the suturing material support structure and finally the application of vacuum by the suction structure is interrupted so that the tissue returns to its original location. This suturing instrument however is only suitable for stitching over closed tissue since only then can it be pulled into the cavity by the suction structure. Suturing of the edges of wounds is not possible.

DE 29 27 143 A1 discloses a surgical instrument for the application of sutures which is designed particularly for the attachment, by stitching, of heart pace makers. This instrument comprises an instrument shaft with a proximal end and a distal end to be inserted into the body of a patient. The instrument shaft includes two channels which receive sections of a wire-like suturing material. At the distal end these channels are shaped in such a manner that the suturing material assumes an annular shape. At the beginning of the operation the electrode of the pace maker is attached to the distal end of the instrument shaft. A two-piece handle portion is used to advance the suturing material and to disconnect the electrode. The instrument has no jaws. It might be utilized for suturing tissue edges but only under most favorable conditions.

U.S. Pat. No. 1,449,087 discloses a plier-like suturing apparatus with two curved jaws at its distal end of which each is provided with a clamping surface. Each jaw includes a curved channel which ends at the clamping surface. By means of a piston a surgical stitching needle with stitching material is moved through the curved channels and through the tissue disposed between the clamping surfaces.

EP-A-0 121 362 discloses a clamping arrangement with opposite clamping jaws of which one includes a channel receiving a straight piece of stiff suturing material and the other has a curved channel into which the suturing material is moved through tissue disposed between the clamping jaws whereby the suturing material is bent to an annular shape.

It is the object of the present invention to provide a suturing instrument without the disadvantages of the known instruments, with jaws which do not penetrate the tissue and which permits the application of several sutures with a single operating procedure. The instrument should permit suturing of wound edges in conventional surgery as well as in minimally invasive surgery. It should therefore be slim enough to be movable and operable through an access sleeve (Trokar sleeve).

SUMMARY OF THE INVENTION

In a suturing instrument for remote suturing of the edges of tissue wherein a stationary and a pivotal jaw are arranged at the distal end of an instrument shaft and a suturing wire guide channel extends through the instrument shaft for supplying a suturing wire from the instrument's proximal end to the stationary jaw and wherein an outer tube is movably disposed on the instrument shaft for engaging the pivotal jaw to move it toward and from the stationary jaw and hold the jaws in an operating position in which they are arranged parallel to one another, the jaws have spaced wire guide grooves with groove bases defining in the operating position of the jaws, a screw line which is followed by the suturing wire when it is advanced by advancing means operated by a handle disposed at the proximal end of the suturing instrument.

With the suturing instrument according to the invention, tissue edges can be fixed after lacerations or incisions. For that purpose the two tissue edges to be connected are placed onto one another by means of grasping pincers or a special arrangement of the suturing instrument according to the invention to be described below in greater detail such that the two surfaces of the tissue adjacent the wound edges are in contact with each other. The sutures are applied while portions of the adjacent tissue are held together in a kind of tissue fold projecting essentially perpendicularly from the surface of the rest of the tissue.

With the jaws of the suturing instrument according to the invention, the edges of the tissue are engaged such that they are disposed closely together. The jaws will assume a position in which they are disposed essentially parallel to one another at a distance which corresponds about to twice the thickness of the tissue to be sutured together. This position will be designated as the operating position in the following description. Depending on the grasping depth single or double row sutures can be applied in the operating position.

Both jaws have formed in their opposite faces, that is, in the movable as well as in the stationary jaw, several spaced grooves which extend from the suturing wire supply channel and whose base surfaces are disposed along a screw line.

When the suturing wire is advanced in the channel it is moved out of the end of the channel in the stationary jaw such that it penetrates the two tissue ends held together by the jaws and then enters the first groove in the movable jaw where it is bent around and (if the grasping depth of the jaws is large enough) again penetrates the tissue ends. Then the tip of the suturing wire enters the first groove in the stationary jaw where the suturing wire is further guided along a screw line.

When the suturing wire has passed all the grooves in the jaws it has a screw-like or spiral shape. The axis of the suturing wire coil is parallel to the tissue edges. Depending on the grasping depth of the jaws the coil penetrates the tissue once or twice with each turn so that a single or double row suture is formed. After completion of the suture the suturing wire is cut and secured to prevent it from sliding out of engagement with the tissue. The procedure is repeated until the tissue edges are sutured over their full length.

Preferably the suturing wire is moved within the channel by suitable design means in a stepwise fashion by means of the handle portion, from the proximal toward the distal end. The length of the advancing steps depends on the strength of the suturing wire utilized. Preferably a thin metal wire of stainless steel, tantalum, etc. is used. Metal wires of this type are sufficiently stiff so that they do not tend to cant or bend; they also are able to penetrate the tissue without any auxiliary means. However the instrument according to the invention may utilize also other types of suturing materials as long as they are sufficiently stiff. The advancing steps should be selected—in accordance with the mechanical strength of the suturing material utilized—such that they are sufficiently short to prevent canting of the suturing material within the supply channel and that it penetrates the tissue without bending; but they should be as long as possible under the given conditions to keep the time necessary for the distal advancing of the suturing material during an operation within reasonable limits. If the suturing material is a stainless steel wire with a diameter of 0.25 mm the single advancing steps may have a length of 3 mm.

Preferably the channel is provided with a locking structure which .engages the suturing wire to prevent the suturing wire from sliding back and which releases the suturing wire for the advancing movement. It is particularly preferred if the locking structure can be controlled by the operator from the operating handle so that the locking mechanism can be operated to release the suturing wire, for example, for replacement of the suturing wire.

The movable jaw should be movable from an operating position toward the stationary jaw and away therefrom. In operating position both jaws are about parallel to one another. Their operating distance is predetermined by design and is determined essentially by the thickness of the tissue, that is, it is essentially twice the thickness of the tissue to be sutured.

The position of the movable jaw in which it is pivoted away from the stationary jaw will be called in the following description the rest position of the jaws. By movement of the movable jaw from the operating position to the rest position and back the tissue layers to be sutured can be grasped and also released.

The possibility to move the movable jaw from the operating position toward the stationary jaw is advantageous for the following reasons:

During the distal advance of the suturing wire while the suturing procedure is in progress, the suturing wire is brought into a screw or spiral shape since, during suturing, the suturing wire which leaves the guide channel terminates within the stationary jaw in which the suturing wire is guided and shaped by the grooves formed in the two jaws. Then, as mentioned, the tissue to be sutured is penetrated either once when the suturing wire front tip passes from the stationary jaw to the movable jaw or also (with sufficient grasping depth) upon passing over of the material front tip from the movable jaw to the stationary jaw. Guiding and shaping the suturing wire and also piercing of the tissue results in friction forces which can become quite large with an increasing number of screw lines or spiral passes.

The friction forces can be greatly reduced by movement of the movable jaw from the operating position toward the stationary jaw. The distance by which the movable jaw is moved for this purpose is preferably only a few tenths of a millimeter. This movement has the result that the diameter of the spiral of the suturing wire is slightly reduced. For this reason the movable jaw is moved slightly toward the stationary jaw at the end of each advancing step by means of the operating handle. In the operating position of the jaws the suturing wire is then not engaged in the grooves too tightly so that, during the following advancing step, the friction is reduced. The friction may also be reduced during advancement of the suturing wire by the application of a suitable lubricant. Such lubricants, for example, silicon oil, are known and are utilized with other suturing instruments presently in use.

By movement of the movable jaw toward the stationary jaw, the finished suture can be position-locked. After completion of the suturing procedure and after cutting the suturing wire the movable jaw is pivoted back to its rest position whereby the tissue and the suture are released. Then the spiral of the suturing wire is grasped with the front ends of the jaws and is compressed wherein the movable jaw is moved toward the stationary jaw until it reaches its operating position. In this manner, release of the suture is prevented.

To facilitate this step an embodiment is preferred wherein the distal ends of the jaws are profiled at their opposite sides in front of the guide grooves. A preferred profile structure consists of closely adjacent recesses which extend parallel to the grooves, that is, which are arranged at the same angle with respect to the axis of the outer tube and at a distance from one another which is 1/n of the distances between the grooves; wherein n is an integral number. With such recesses the completed spiral structure of the suturing wire can be grasped especially securely since the windings of the spiral are received in these recesses and are supported therein so that the spiral is safely held and can be deformed in a controlled manner.

Depending on the embodiment chosen for the suturing instrument according to the invention it may be advantageous to provide the outer tube at its distal end with two opposite recesses. These recesses are arranged in such a way that, upon distal axial movement relative to the instrument shaft and consequently to the jaws with the tissue engaged thereby, the outer tube will not come into contact with the tissue and therefore will not damage the tissue. Such recesses are preferably arranged symmetrically with respect to a plane which extends parallel to the side of the stationary jaw which is disposed opposite the movable jaw. The shape of the recesses may greatly vary depending on the shape of the suturing instrument. The outer tube may, for example, by chamfered at its distal end in such a way that the stationary jaw is not fully surrounded thereby.

Furthermore the distal end of the outer tube and the edges of the recesses can be rounded in order to further reduce the chances of damaging the tissue.

Advancement of the suturing wire during suturing is facilitated if the ends of the grooves which are first reached by the suturing wire are widened in a funnel-like fashion. This prevents canting of the suturing wire and guides the suturing wire into the grooves.

After completion of a suture the suturing wire can be severed by means of a slide with a cutting edge which is arranged in the stationary jaw and which can be operated from the proximal end of the instrument by way of a lever.

Preferably, the movable jaw is moved from the operating position away from the stationary jaw in the following manner: Within the outer tube the movable jaw is provided with a V-shaped structure directed with its pointed edge toward the stationary jaw. The pointed edge of the V-shaped structure extends transverse to the axis of the outer tube and is supported in a recess in the stationary jaw, which also extends laterally with regard to the axis of the outer tube. At the distal end of the outer tube a pin is provided on its side opposite the stationary jaw in such a manner that, by sliding the outer tube toward the operator relative to the jaws, the distal side surface of the V-shaped structure is moved toward the operator whereby the pointed edge rotates in the recess and the movable jaw moves away from the stationary jaw. The outer tube is axially movable relative to the instrument shaft by means of the handle at the proximal end.

The movement of the movable jaw toward the stationary jaw is preferably achieved by sliding the outer tube in the distal direction over the movable jaw. In this manner, again the operating position, that is, parallel positioning, of the jaws is achieved. The further movement of the movable jaw toward the stationary jaw is preferably provided for by a protrusion on the outer surface of the movable jaw which is engaged by the outer tube upon further movement thereof in distal direction.

One of the jaws of the suturing instrument according to the invention, for example, the stationary jaw, may carry on its side opposite the other jaw a pointed thorn which, in the operating position of the jaws, is received in a correspondingly shaped cavity in the other jaw.

With an instrument modified in this manner the use of grasping pincers for grasping the tissue edges during the suturing procedure is not necessary. In the rest position of the jaws the thorn is placed under the first tissue edge at a suitable location. For engagement of the tissue by the thorn the jaws are moved to their operating position whereby the tissue is perforated by the thorn. Then the movable jaw is again lifted (moved to its rest position) and the second tissue edge is engaged in the same manner. If the thorn is arranged at the proximal end of the jaws, for example, behind the opening of the channel for the suturing wire, only one additional penetration per suturing procedure is required. If the thorn is arranged at the distal end at the pointed end of the jaws, better sight conditions facilitate the grasping of the tissue edges. In this case, however, another penetration of the tissue is necessary during the final deformation of the spiral suturing wire.

The invention will be described in greater detail on the basis of figures in which a particular embodiment of the surgical suturing instrument according to the invention is shown.

DESCRIPTION OF THE PREFERRED EMBODIMENT

The embodiment of the invention illustrated is designed for a suturing wire consisting of stainless steel wire with a diameter of 0.25 mm. It comprises three building groups:

the operating head with the jaws 23, 24 and the severing device 45 for the suturing material 17, the handle 1, 2 comprising the handle head 18 with the stationary hand portion 2 mounted thereon and the movable finger portion 1 which is movable relative to the stationary hand portion 2, and the instrument shaft 20 which is mounted on the handle 1, 2 and locked thereto by a clamping screw 10 and which interconnects the jaws 23, 24 and the handle portion 2 as well as the outer tube 21 for operating the movable jaw 24 by means of the finger portion 1.

Further, the following functions are identifiable with various parts for the mechanical realization which parts are present in all three building groups:

acknowledgement of the movable jaw 24, for the embodiment with an additional thorn: engagement and combining of the tissue edges, forming of the suturing wire 17 into a spiral 26, reduction of the diameter of the spiral of the suturing wire 17, for example, after each advancing step for the reduction of friction between the suturing wire and the shaping guide grooves 38 in the jaws 23, 24, repeated clamping and subsequent stepwise advancing of the suturing wire 17 by the advancing structure 14, 28, self-locking arresting of the suturing wire 17 against retraction of the wire to its start position in the locking device 57, 58 and during repositioning of the clamping and advancing arrangement 14, 28, severing of the suturing wire, taken for example from a roll, at the end of a suturing procedure by means of a movable severing slide 45, bending of the suturing wire 17 at the beginning and end of a suture toward the tissue in order to inhibit retraction of the suturing wire into the tissue upon opening of the movable jaw 24 to prevent opening of the suture before its securing;

forming of the suturing wire front end upon severing so that the penetration forces are minimized and, upon penetration of the tissue, a guiding force is generated at the front end of the suturing wire which is directed toward the axis of the spiral, shaping of the originally circular suturing wire spiral cross-section into a flat oval shape to prevent opening of the suture, securing of the severing mechanism 45 against unintended operation, and modifying the function sequences by various control knobs 15, 16 with predetermined operation of the handle 1, 2.

The distal end of the outer tube 21 with the instrument shaft 20 received within is introduced into the body of a patient through an access sleeve. For this purpose the movable jaw 24, which, in its rest position, is pivoted away from the stationary jaw, is pivoted by actuation of the finger portion 1 of the handle 1, 2 and the resulting translatory movement of the outer tube 21 to its operating position parallel to the stationary jaw 23.

Because of an adjustable play in the coupling mechanism all other instrument functions are not activated by the jaw pivoting step.

The design of the instrument is such that, for facilitating an exact manipulation in the surgery area, the distance between the hand-held stationary handle portion 2 and the two jaws 23, 24 remains constant. For the operation of the movable jaw 24 only the outer tube is moved axially so that no compensating hand movement by the surgeon is needed for maintaining the desired spatial location of the jaws 23, 24.

The distal end of the instrument comprises the two jaws 23, 24. The stationary jaw 23 is made by giving the distal end of the instrument shaft on appropriate shape (FIGS. 1 and 6, 6a–c).

Figures 3A, 3C:
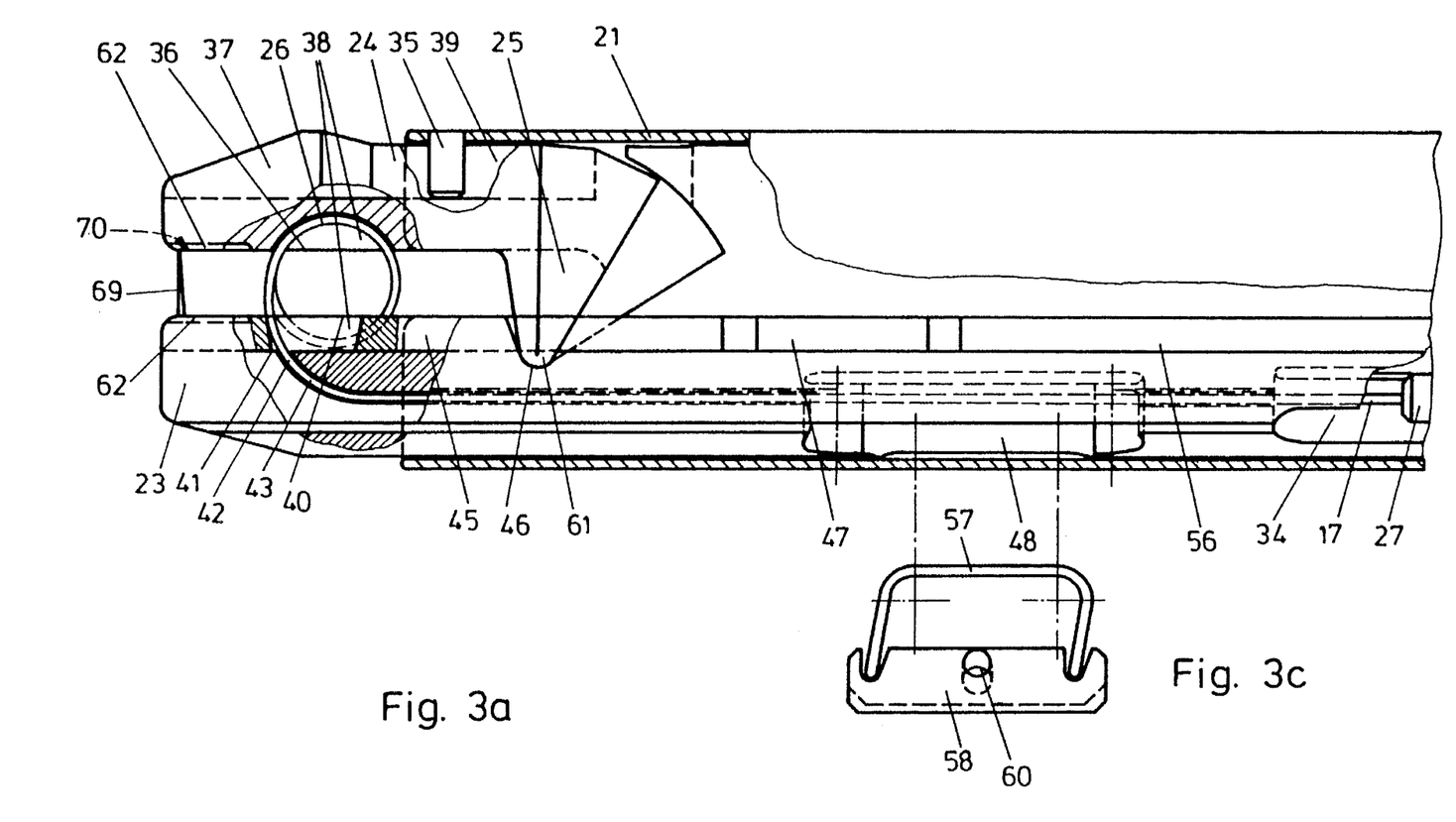
FIG. 3a shows the distal end of the instrument with the jaws and the locking device.
FIG. 3c shows a locking structure for the suturing wire.
Figure 3B:
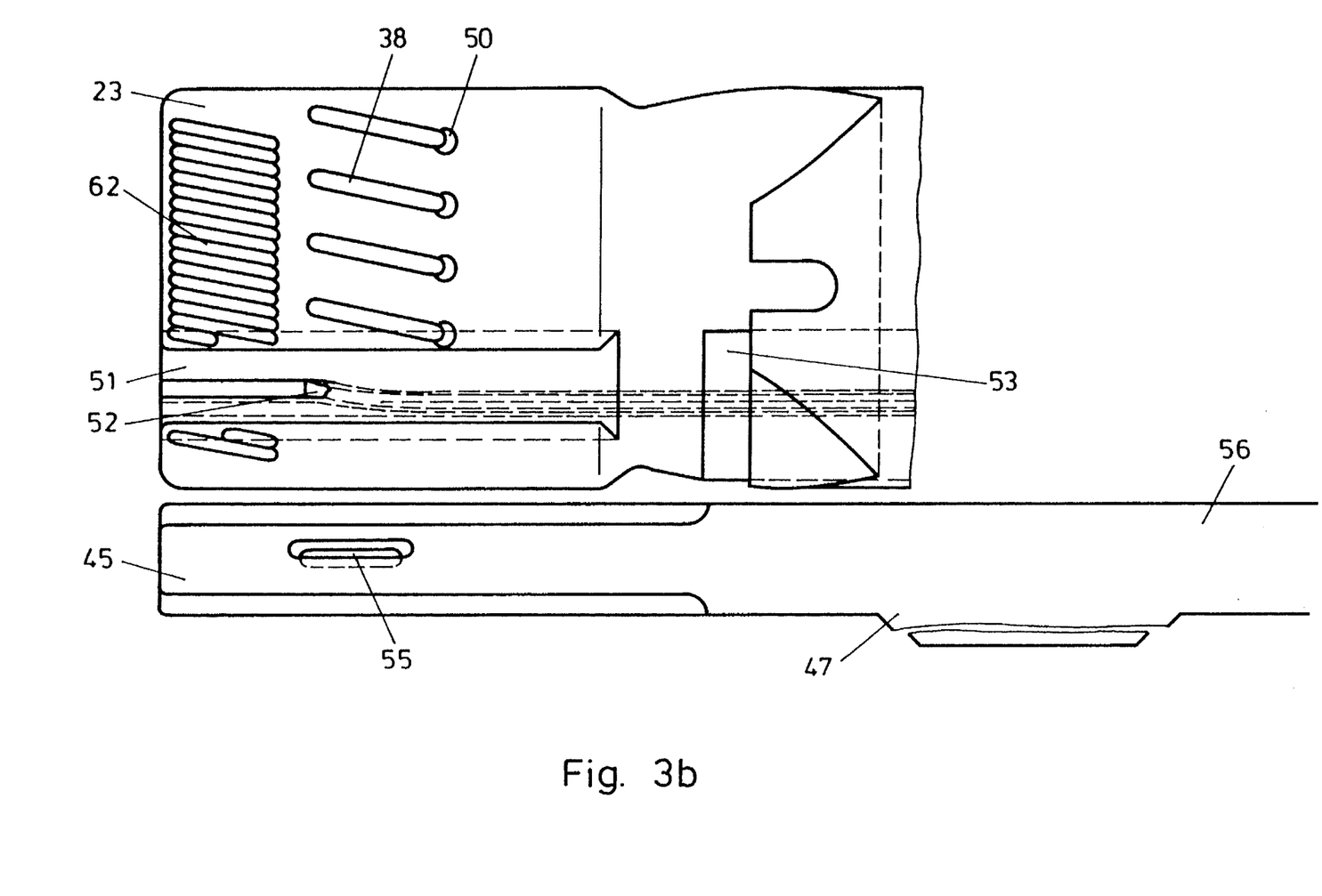
FIG. 3b is a top view of the stationary jaw with the movable portion of a severing device.

The design of the jaw 24 and the guide structure for the suturing wire 17 are apparent from FIGS. 3a and 3b.

The pivot bearing portion 61 of the second movable jaw 24 is disposed in a recess 46 of the instrument shaft 20 behind the stationary jaw 23.

The movable jaw 24 is pivoted open by a pin 35 extending inwardly from the outer tube 21 which is movable in a slot 39 in the instrument shaft 20 and it is pivoted to the closed position by sliding the upper distal front edge of the outer tube 21 over the outer jaw surface. The outer tube 21 has recesses 25 to accommodate tissue received between the jaws during such movement. The movable jaw 24 is held in position relative to the stationary jaw 23 only by its shape, that is, its reception in the recess 46 of the instrument shaft and its being held therein by the outer tube 21. No pins or connecting and support bolts were used since, because of the small dimensions they would be difficult to mount and would be often overloaded.

As already mentioned the two superimposed tissue edges are engaged by the jaws 23, 24 in such a manner that there will be only one penetration row right behind the edges and the suturing wire passes, on the other side, outside the tissue or that, with greater depth engagement by the jaws 23, 24, two parallel penetration rows are generated and the suturing wire is exposed only at the upper and lower side of the suture.

Figure 1:
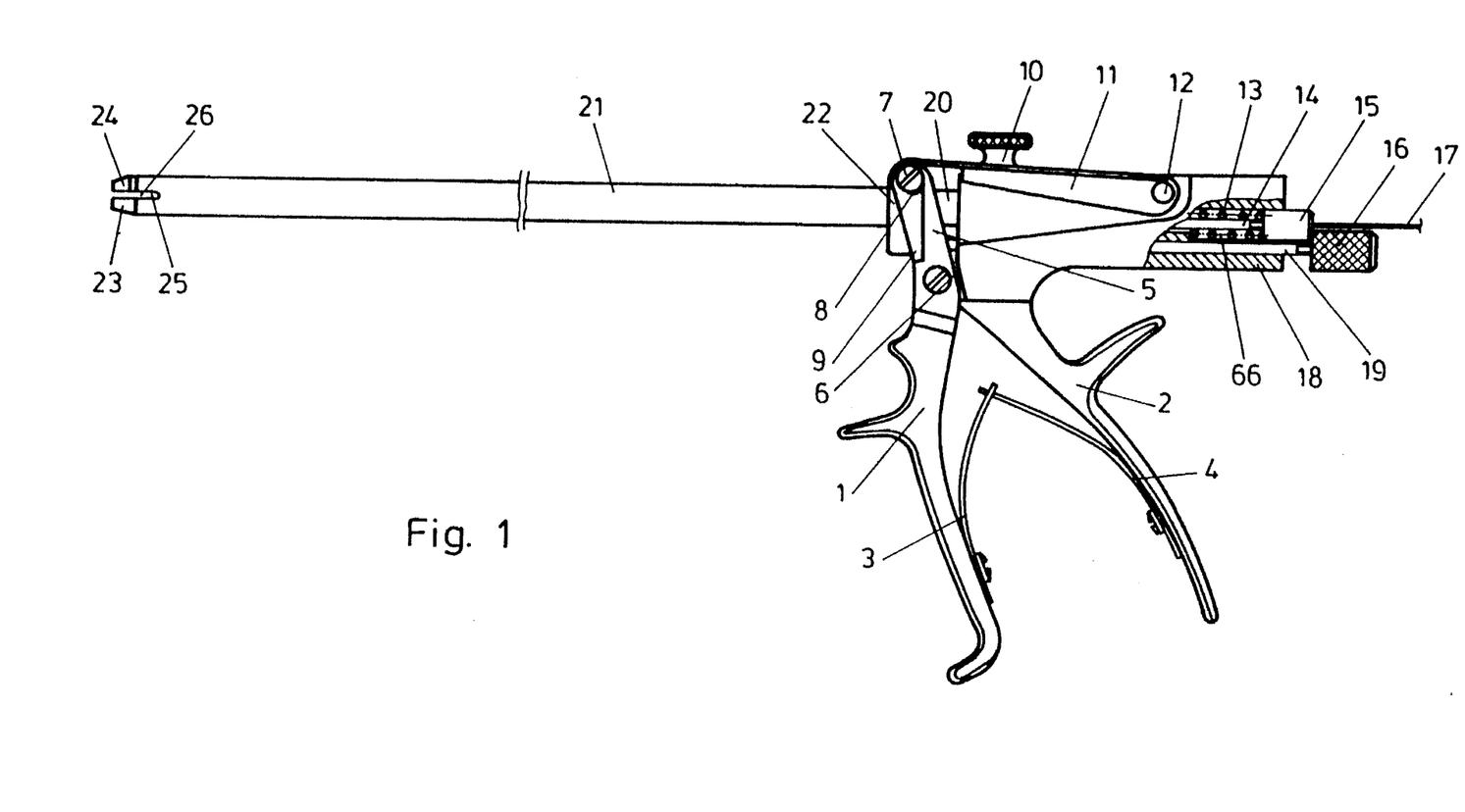
FIG. 1 is a complete view of the suturing instrument according to the invention.

The screw-like suture spiral is generated in a stepwise fashion by multiple actuation of the handle 1, 2 (FIG. 1). The circular spiral has, with a suturing wire cross-section of 0.25 mm, an outer diameter of 4 mm.

By means of a wire engagement and advancing mechanism 14, 28 (see FIG. 2) to be described below the wire is moved through the guide channel 43 in the stationary jaw 23 by further operation of the handle 1, 2. The wire is advanced in a stepwise fashion by 3 mm with each step.

The suturing wire 17 first passes through a slot 55 (FIG. 3b) adapted to the spiral pitch which slot is disposed in the movable severing slot 45 in the stationary jaw 23.

In the area of the guide channel 43 which is disposed in the stationary jaw 23 and in the movable severing slide 45 the wire 17 is bent accurately in a plane parallel to the instrument axis. The radius of the arc is, for space reasons (the severing slide 45 has to be accommodated in the stationary jaw 23) somewhat larger than the finished spiral so that final shaping of the wire 17 is achieved only after the first tissue penetration within the movable jaw 24.

At the end of each wire advancing and forming step the distal end of the outer tube 21 is moved onto a projection 37 eccentrically disposed on the outer surface of the movable jaw 24 whereby the jaws are forced further together by 0.3 mm. This results in a reduction of the suture spiral diameter by a corresponding amount.

This step is necessary in order to prevent locking of the spiral wire within the guide grooves 38 of the jaws 23, 24 as a result of friction forces based on the condition $$S_2 = S_1 \times \exp(\mu\alpha) \tag{1}$$

wherein:

$S_2$=the advancement force for the wire [N];

$S_1$=the friction and resistance force at the front end of the wire [N];

=the friction coefficient between wire and guide groove [–];

=the contact angle of wire and guide groove [rad]. (The friction of the wire within the tissue is disregarded in equation (1).)

In order to facilitate the insertion of the front end of the wire into a guide groove after penetrating the tissue the entrances 50 of the guide grooves 38 are widened conically (see FIG. 3b).

For a full or partial completion of the spiral suture 26 z operating steps with the jaws arranged in parallel are required. The number z is a function of the desired suture length and the desired number of stitches or windings and the selected step length of the wire advancing steps.

At the end of each partial suture the handle 1, 2 is pulled back to the stop of the operating area for spiral compression. Then the lever 11 of the handle head 18 (see FIG. 1) which can be reached by the thumb of an operator is released for actuation. By pushing this lever 11 down the movable severing slide 45 is moved in the dovetailed groove 51 of the stationary jaw 23 in proximal direction whereby the wire 17 is severed in the severing slot 55 between the cutting edges 41 and 42 and the spiral end is bent by the rounded upper edge of the slide 45 into the plane of the inner surfaces 36, 40 of the jaws.

This measure, like a corresponding wire deformation at the front end serves to secure a completed suture so that the spiral does not turn open after the movable jaw 24 is pivoted back for repositioning of the jaws 23, 24 for example. Such repositioning is provided for in order to deform the circular spiral cross-section in the forming area of the front portion of the jaws to a flat-oval shape such that opening of the suture is essentially impossible.

Upon severing of the wire 17 at the end of the spiral, the front end of the wire is, as a result of the shape of the cutting edge 52 in the stationary jaw (two cutting edges at an angle of 60° relative to one another) shaped in such a manner that the penetration resistance of the wire in the tissue is as small as possible, and during tissue penetration a force component in the direction toward the spiral axis is generated, which counteracts radial outward movement of the wire 17 as a result of the outward bending moment generated by the penetration resistance forces.

As already described the instrument shaft 20 is disposed within an outer tube 21 which is movable in axial direction by operation of the handle 1, 2.

In the instrument shaft 20 (see FIG. 6) which, at the distal end, forms a stationary jaw and is shaped so as to support the movable jaw, there are provided the longitudinal grooves 51, 53 for receiving and guiding the movable slide 45 and a connecting rod 56 for operating the slide of the severing structure and further the longitudinal groove 34 for guiding the support tube 27 for the suturing wire 17. Further the instrument portion comprises in the square guide channel 43 for the wire—in advancing direction closely in front of the stationary jaw—a pocket 48 for the reception of a spring-loaded locking pad 58 provided with a bore 60 for engaging the locking pad 58 to move it out of its locking position if the wire is to be retracted.

Since for space reasons the wire engaging and advancing mechanism 14, 28 (see FIG. 2) is disposed in the handle head 18 of the instrument, provisions must be made to prevent kinking of the suturing wire (with a diameter of 0.25 mm) when it is advanced through the instrument shaft 20 up to the end of the guide channel 43 in the stationary jaw 23. For this reason it is supported during its advancement in a wire support tube 27 (FIGS. 2, 3a) with an outer diameter of 1.5 mm so as to remain free of kinking. The wire support tube 27 is welded together with the clamping sleeve 28 of the advancing mechanism and is moved back and forth in the groove 34 of the instrument shaft 20 in accordance with the selected step length.

Figure 2:
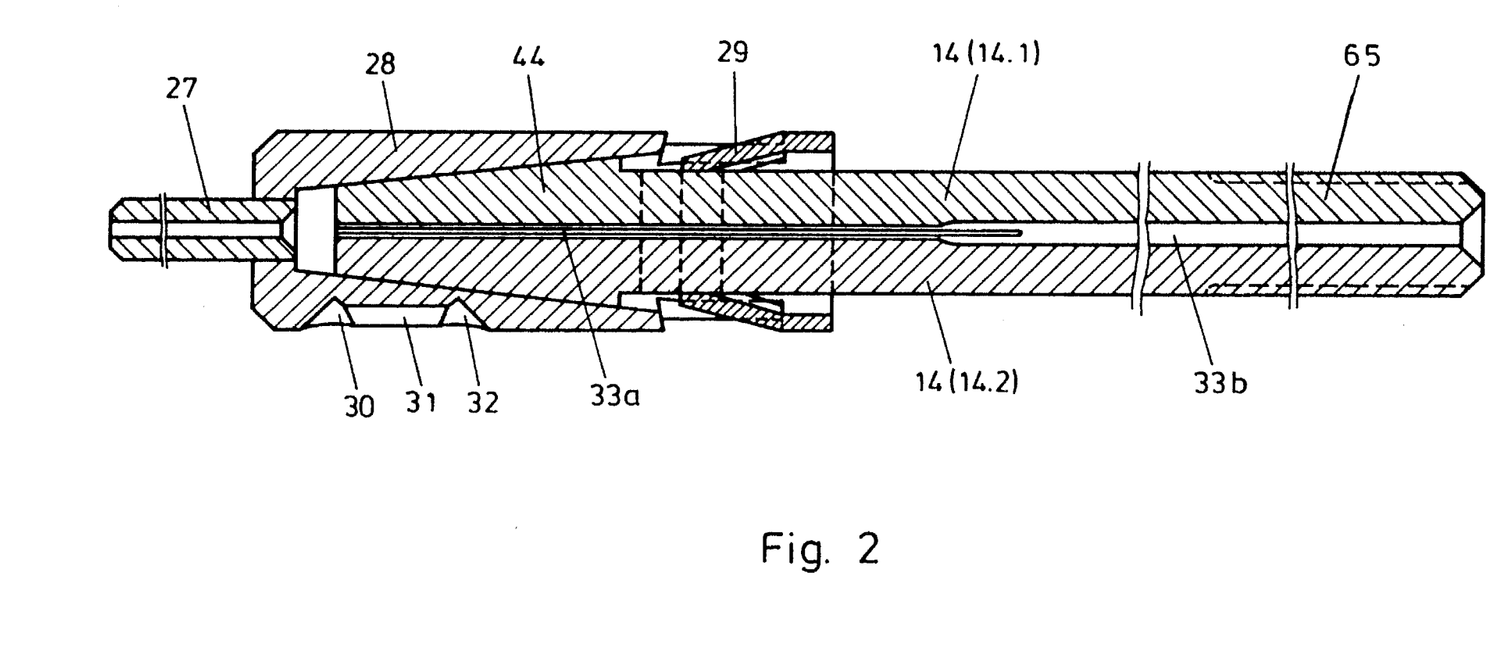
FIG. 2 shows the supply channel for the suturing wire with an arrangement for advancing the suturing wire.
Figure 4:
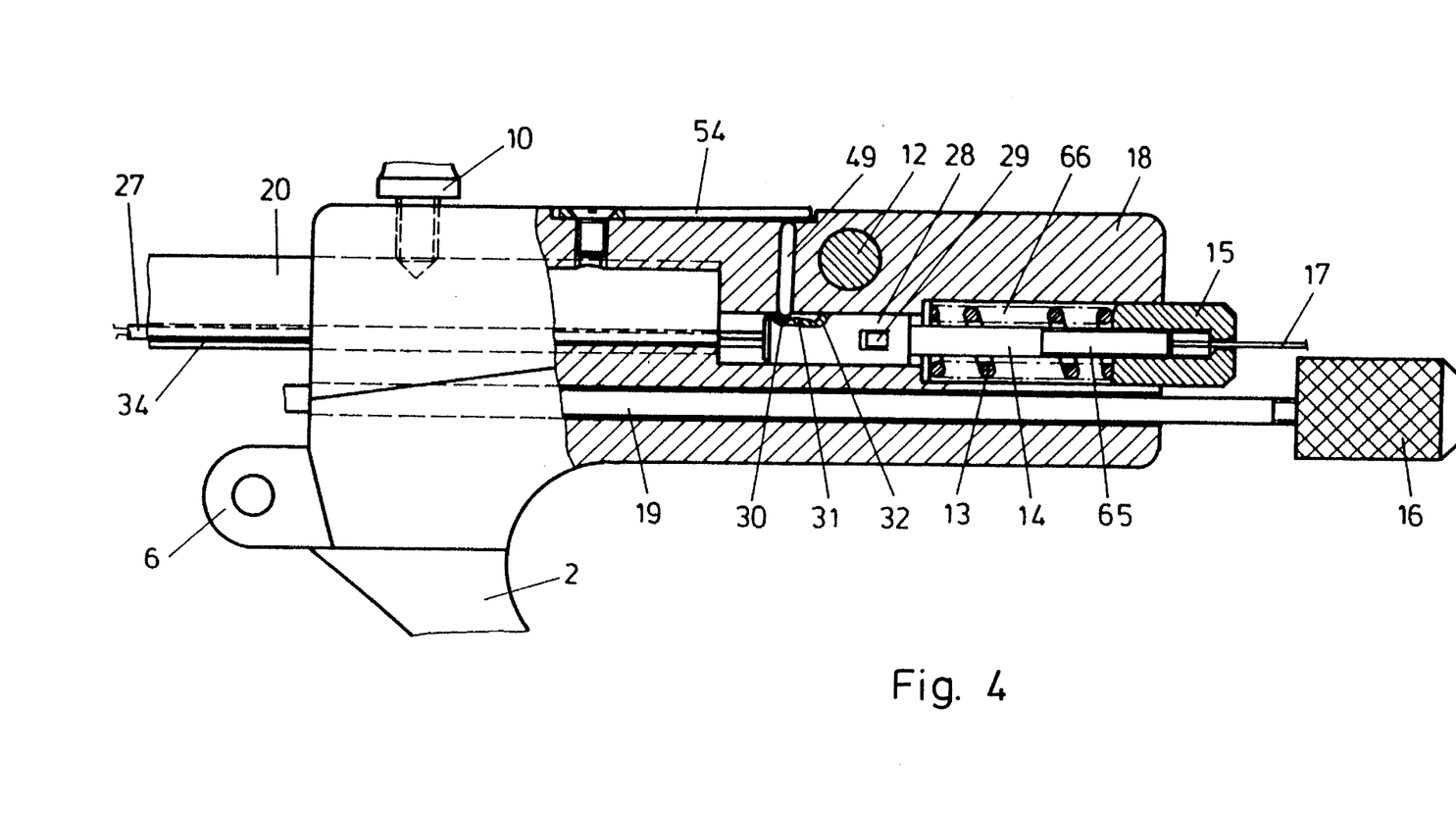
FIG. 4 is a partial sectional view of the grasping head.

Upon retraction of the support tube 27 the spring-loaded locking pad 58 (FIG. 3a) which then engages the suturing wire prevents the pull-back of the suturing wire 17 which might otherwise happen because of friction on the inner wall of the support tube and in the clamping structure 14 (FIGS. 1, 4 or 14.1, 14.2 in FIG. 2).

The surgeon can—for example, for exchanging the suturing wire 17—couple the locking pad 58 and the outer tube 21 by means of a pin extending through the bore 60 in the locking pad 58 and a corresponding bore in the outer tube and he can eliminate the engagement between these two parts by actuating the operating handle.

Figure 7:
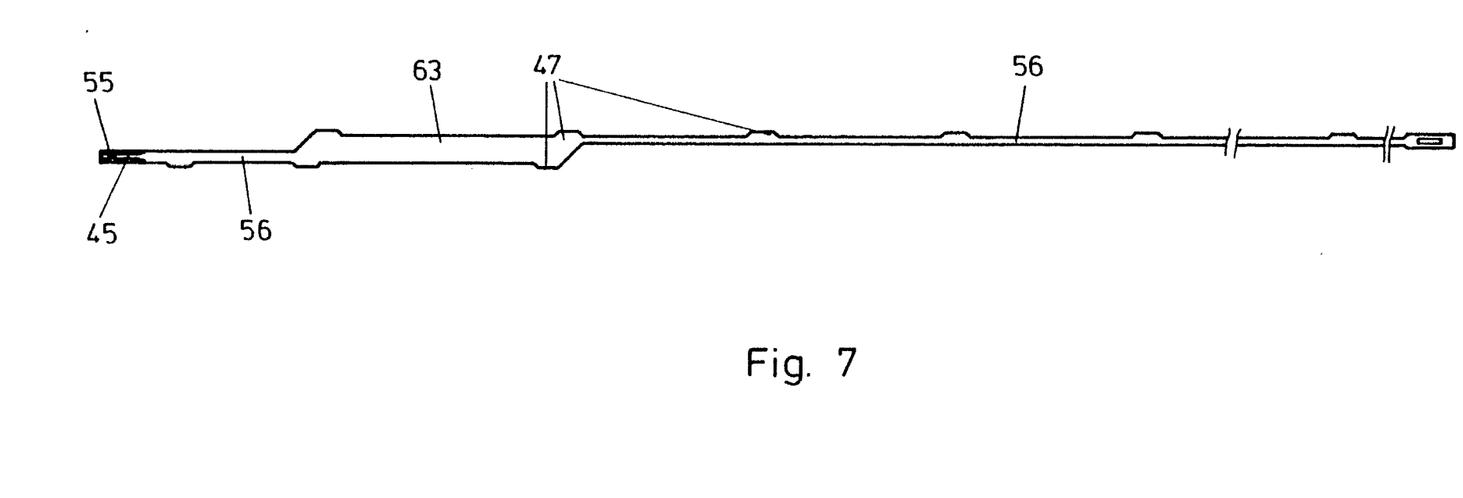
FIG. 7 shows the severing device.

The movable slide 45 and the connecting rod 56 (FIG. 3b, FIG. 7) of the slide drive are made as one-piece structures from partially hardenable stainless steel sheets. Because of the geometric conditions in the handle head 18 a displacement of the connecting rod 56 is provided for which results in a side switch-over from the upper part of the slide 45 in the stationary jaw 23 to the slide drive within a pocket 59 of the handle head 18. The relatively long section 63 in the connecting rod 56 (FIG. 7) is of increased thickness in order to be able to compensate for transverse moments occurring during loading by small support forces between the guide cams 47 of this portion and the inner wall of the outer tube 21. The transverse passage 64 (FIG. 6b) for this increased thickness section is enlarged in proximal direction by the length of the dovetail groove 51 in the stationary jaw 23.

Figure 5:
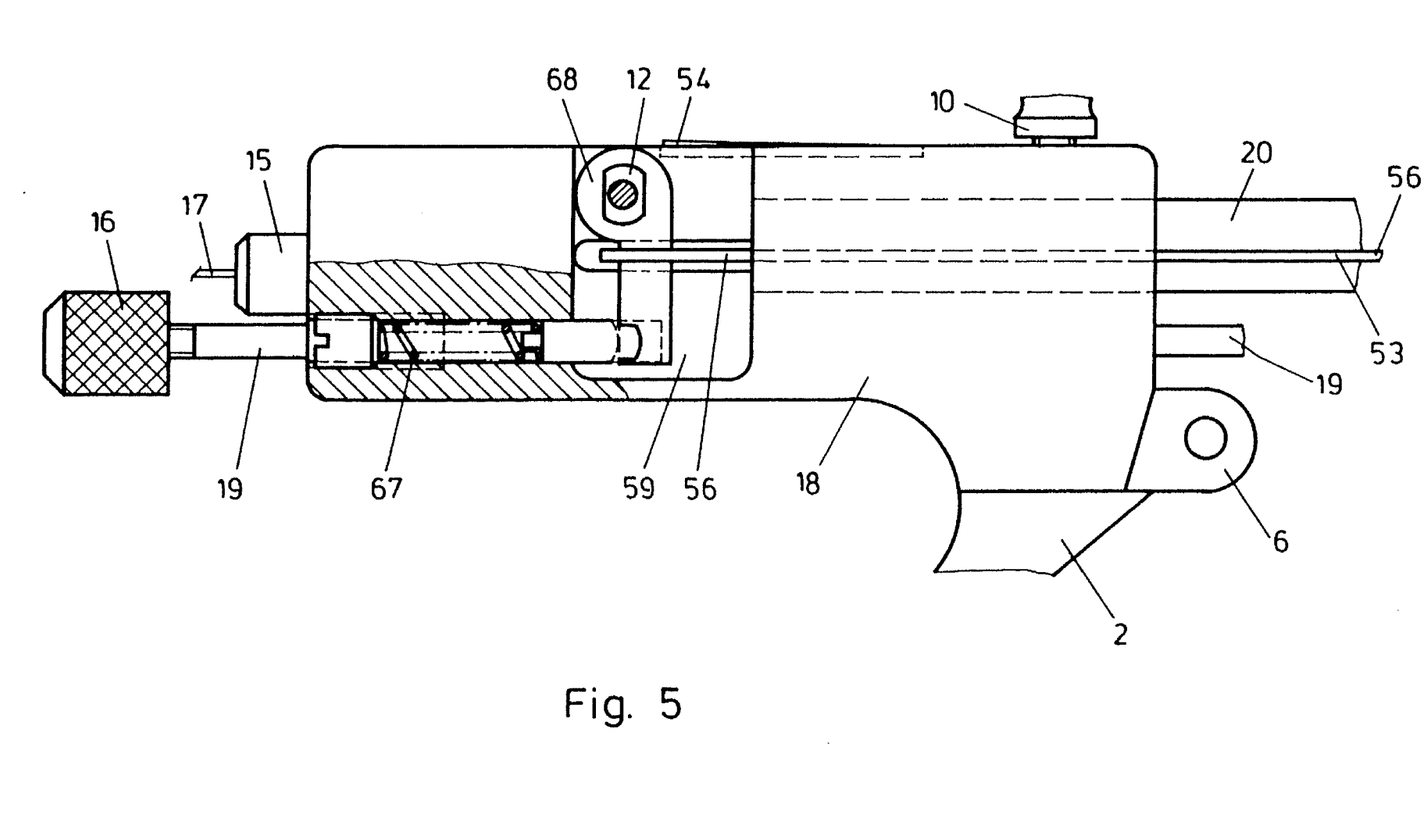
FIG. 5 is another view of the grasping head.
Figure 6:
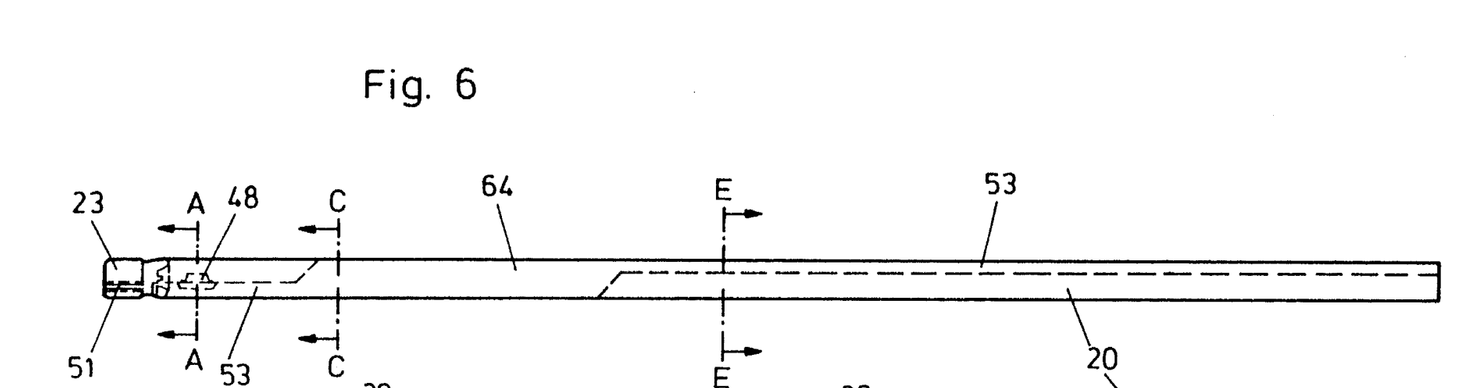
FIG. 6 shows the instrument shaft.
Figure 6A:
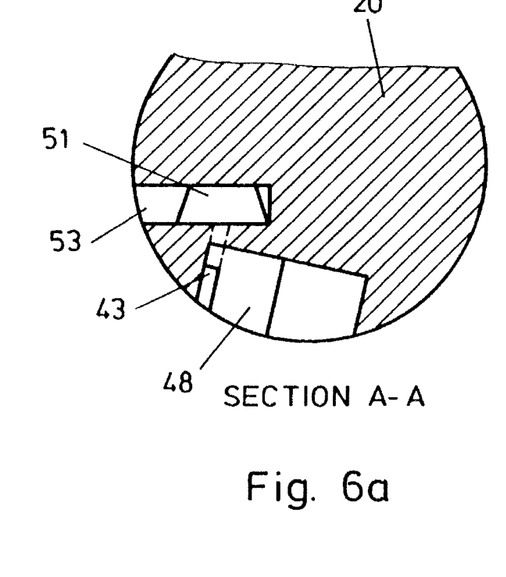
FIGS. 6a, 6b and 6c are enlarged cross-sectional views of the shaft at different locations.
Figure 6B:
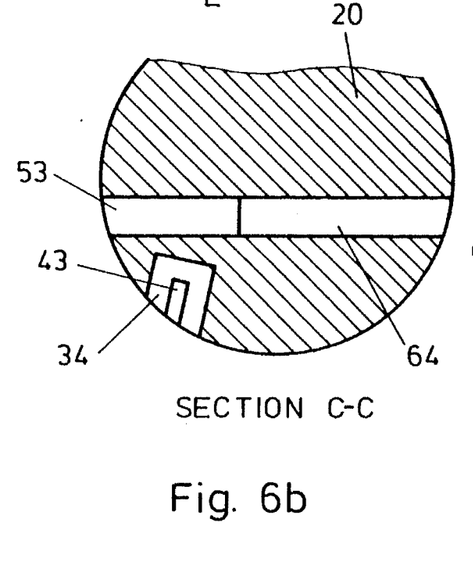
Figure 6C:
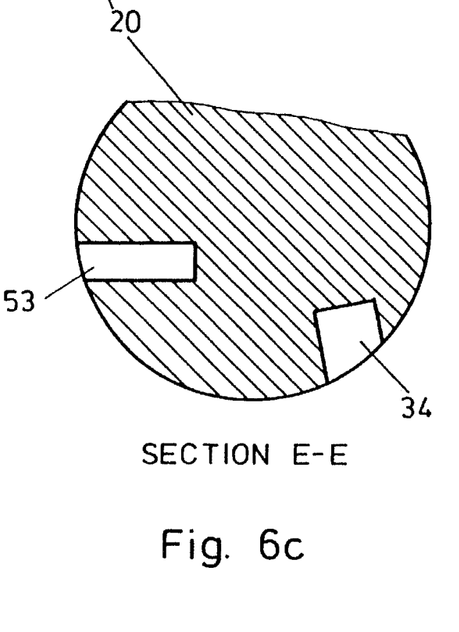

The handle 1, 2 (see FIGS. 1, 4 and 5) of the suturing instrument consists of the handle head 18, the finger portion 1 movable relative thereto, and the hand portion 2 which is rigidly connected to the instrument shaft 20 by means of the handle head 18.

Both handle portions 1, 2 are spread as usual by leaf springs 3, 4 arranged therebetween in the usual manner so that, in their rest positions, they are spread to the maximum extent.

The handle head 18 serves to pivotally support the finger portion of the handle, to accommodate the engagement and advancement mechanism 14, 28 for the suturing wire 17, for the installation of the slide operating mechanism, and for the interconnection of the hand portion 2 of the handle with the instrument shaft 20.

The finger portion of the handle has the usual shape so that it can be grasped conveniently. The upwardly extending fork 5 is pivotally mounted to the handle head 18 by a bearing structure with a bearing pin 6. The upper ends of the fork 5 are further hinged by screws with stepped shafts to the rectangular flange 22 which is welded to the proximal end of the outer tube 21. The shafts of the screws 7 slide in elongated passages 8 at the end of the fork when the outer tube 21 is moved axially. The fork side adjacent the thumb-operated lever 11 is partially thickened and provided with a blocking arm 9 which, in the normal operating range of the handle 1, 2, serves as a safety device against unintended operation of the movable slide 45.

Movement of the rectangular flange 22 (and the outer tube 21) is transmitted to the engagement and advancement mechanism 14, 28 for the suturing wire 17 via a coupling bar 19 guided in the handle head 18. By an exactly adjustable play-length (control knobs 15 and 16) a force is transmitted to the engagement sleeve jaws 14.1, 14.2 only after the movable jaw 24 has reached the parallel operating position by a short initial movement of the outer tube 21.

The engagement and advancement mechanism (see FIG. 2) comprises two main components:

the outer clamping sleeve 28 with a conical opening and two inwardly bent driving lugs 29 as well as the wire support tube 27 welded coaxially to the front end of the clamping sleeve for supporting the wire 17, and the inner engagement sleeve 14 with the slotted cone 44 forming engagement jaws 14.1, 14.2 for frictionally engaging the wire 17 and the longitudinally divided thread portion 65 for applying the advancement forces.

Both parts are disposed within a stepped bore 66 in the handle head 18 in axial alignment with the wire guide channel 43, 14 which extends through the interior of the instrument shaft 21.

On its outside the clamping sleeve 28 is provided with two conical bores 30, 32 which are spaced from one another in longitudinal direction by 3 mm and between which a triangular groove 31 of lesser depth extends. A pin 49 engaged by a leaf spring 54 engages and firmly locates the clamping sleeve 28 in the handle head 18 in accordance with the conical bores 30, 32 in the clamping sleeve 28 in which the pin is received. Upon sliding the clamping sleeve 28 in axial direction, the spring-loaded pin 49 slides through the groove 31 between the bores 30, 32 thereby preventing rotation of the clamping sleeve 28 and, consequently, undesirable torsion of the wire 17. The distance between the bores 30, 32 determines the length of the wire advancing step. Other control structures with different bore distances can be provided side-by-side on the sleeve for different step lengths. Then shorter or longer advancing steps can be provided for simply by rotating the sleeve so that the pin enters another guide groove in which the conical bores are differently spaced.

The engagement structure 14 is first divided in an axial plane. After cutting the prismatic (V-shaped) inner grooves 33a, 33b along the axis of the engagement structure 14, the two halves 14.1, 14.2 are again welded together. The cone section 44 and the threaded portion 65 may be slightly bent open to insure the release of the wire in the clamping area 33a or to achieve frictional engagement of the control knob 15 on the threaded portion 65.

Between the control knob 15 (FIG. 4; for fine adjustment of the force of spring 13) on the threaded portion 65 of the engagement structure 14 and the shoulder of the stepped bore 66 receiving the advancing mechanism 14, 28 (see FIG. 2) a strong coil spring 13 is disposed, which, in rest position of the instrument, forces the engagement jaw structure 14 outwardly so as to disengage the cone section 44 from the wire 17 and which retracts the clamping sleeve 28 such that the spring-loaded pin 49 snaps into the distal conical bore 30 in the clamping sleeve 28.

Upon actuation of the handle 1, 2 out of its rest position first the movable jaw is pivoted to a position parallel to the stationary jaw—as described earlier. Then the control knob 16 for adjusting the free play which is disposed on the coupling bar 19 in the handle head 18 engages the clamping jaw structure 14. The cone section 44 of the clamping jaw structure 14 is then moved into the clamping sleeve 28 where it is compressed and firmly engages in the prismatic channel 33a the suturing wire 17 admitted through the central passage in the control knob 15. With further increase of the advancing force the pin 49 in the handle head 18 is lifted out of the distal bore 30 in the clamping sleeve 28 against the force of the leaf spring 54 and the clamping sleeve 28 with the support tube 27 is advanced.

The clamping sleeve 28 including clamping jaw structure 14 and suturing wire 17 are moved—prevented from rotation by the pin 49 which is guided in the triangular groove 31 between the bores 30, 32—in distal direction up to the end of the advancing step where the pin 49 snaps into the conical bore 32 of the guide structure 30, 31, 32.

In this position the front edge of the outer tube 21 is moved onto the eccentric transverse projection 37 of the movable jaw 24 whereby the diameter of the wire spiral is reduced.

When the force applied to the handle is reduced the handle parts are moved apart by the leaf springs 3, 4 disposed therebetween. The outer tube is then retracted on the instrument shaft 20 in proximal direction.

The tensioned clamping structure spring 13 then pulls the clamping structure 14 out of the conical cavity of the clamping sleeve 28 which is still held in position by the locking pin 49 thereby releasing the suturing wire 17. When the driving lugs 29 are engaged the force of the spring 13 is applied also to the clamping sleeve 28. Then the pin 49 is dislodged from the conical bore 32 and the clamping sleeve 28 moves past the pin 49 which slides through the triangular groove 31 until it snaps into the distal bore 30.

Retraction of the suturing wire 17 during this procedure by the friction between the wire and the wire support tube 27 is prevented by the locking pad 58 which engages the wire so as to permit only advancing movement thereof.

From the position now achieved—with the jaws 23, 24 arranged in parallel—a further wire advancing step can be initiated by another actuation of the handle 1, 2 and another return step of the wire advancing mechanism 14, 28 by again releasing the handle.

After about 16 to 17 cycles about 4 suture windings are completed. Then, with the handle fully compressed, the lever 11 is pushed down with the thumb of the hand holding the handle whereby the suturing wire is severed at the spiral end.

After retraction of the movable slide 45 by a lever 68 which is mounted on a shaft 12 and biased by the spring 67, the handle 1, 2 can be opened up to its final stop whereby the movable jaw is moved to its rest position.

After repositioning the instrument slightly, the jaws 23, 24 can again be closed for deforming the spiral to an oval-flat shape in the front part of the jaws. The closing movement of the jaws to achieve this takes place only within the play range, that is, without activation of the wire clamping and advancing mechanism.

To facilitate the process of deforming the spiral suture the inner jaw surfaces 36, 40 at the distal end of the jaws 23, 24 are profiled by grooves 62 extending parallel to the portions of the suture wire to be engaged thereby.

Finally it is noted that a thorn 69 may extend from the stationary jaw 23 and extend into a recess 70 in the pivotal jaw 24 for firmly holding tissue between the jaws 23, 24.

What is claimed is:

1. A suturing instrument comprising an instrument shaft having a distal end for insertion into the body of a patient and a proximal end at the opposite end of said instrument shaft, two oppositely disposed jaws arranged at the distal end of said instrument shaft, the first one of said jaws being firmly connected with said instrument shaft, and the second of said jaws being pivotally supported so as to be movable relative to said first jaw, said instrument shaft including a guide channel for supplying a suturing wire from its proximal end to its distal end which channel ends in the stationary jaw opposite said pivotal jaw, said instrument shaft further including an outer tube which is axially movable on said instrument shaft and which extends from the proximal end to the distal end of the instrument shaft but leaves the front ends of the jaws exposed, said outer tube engaging said pivotal jaw for pivoting said pivotal jaw by axial movement of said outer tube relative to said instrument shaft between a rest position in which said pivotal jaw is pivoted away from said stationary jaw and an operating position in which said pivotal jaw is disposed essentially parallel to said stationary jaw, said jaws having formed in their opposite jaw surfaces a number of spaced wire guide grooves with groove bases which, in the operating position of the jaws, together define a screw line having a start at the end of said wire guide channel in the stationary jaw for leading said suturing wire through said grooves in said jaws when said suturing wire is advanced through said wire guide channel, and a multipart handle at the proximal end of said instrument shaft for operating said pivotal jaw, one part of said handle being connected to the proximal end of said instrument shaft and another part of said handle being connected to said outer tube for moving said outer tube relative to said instrument shaft by actuation of said handle.

2. A suturing instrument according to claim 1, wherein a suturing wire engagement and advancing mechanism is provided for moving the suture wire by actuation of said handle in a stepwise fashion through said guide channel toward the distal end of said instrument shaft and, upon leaving the guide channel, enters a first of said grooves in said stationary jaw and then alternately in the respective grooves in said pivotal and stationary jaws.

3. A suturing instrument according to claim 2, wherein a locking structure is provided in said guide channel which permits advancing movement of said suturing wire but position-locks said suturing wire when the wire engagement and advancing mechanism is returned between the suturing wire advancing steps.

4. A suturing instrument according to claim 1, wherein said pivotal jaw is movable, by actuation of said handle, from said operating position in which said pivotal jaw is parallel to said stationary jaw, not only away from said stationary jaw but also further toward said stationary jaw.

5. A suturing instrument according to claim 1, wherein said outer tube has, at its distal end, two opposite recesses arranged in alignment with the space formed between the jaws when they are disposed in operating position to provide room for the tissue received between said jaws.

6. A suturing instrument according to claim 1, wherein said jaws are provided at their distal front ends at opposite sides with wire engagement grooves which are disposed closely adjacent one another and extend parallel to the wire guide grooves in said jaws.

7. A suturing instrument according to claim 1, wherein said suturing wire guide grooves in said jaws have funnel-like entrance ends for guiding the suturing wire into said guide grooves.

8. A suturing instrument according to claim 1, wherein said stationary jaw includes a slide with a cutting edge for severing the suturing material.

9. A suturing instrument according to claim 4, wherein said pivotal jaw is provided with a bearing portion which is V-shaped in cross-section and has an edge extending normal to the axis of the outer tube and projecting toward said stationary jaw into a recess extending also normal to the axis of the outer tube and being pivotally supported in said recess, and the distal end of the outer tube is provided with a pin engaging said pivotal jaw such that movement of the outer tube in proximal direction relative to the instrument shaft causes pivoting of the pivotal jaw away from the stationary jaw.

10. A suturing instrument according to claim 4, wherein said pivotal jaw is provided at its surface remote from said stationary jaw with a transverse projection adapted to be engaged by said outer tube when moved fully in distal direction for moving said pivotal jaw toward said stationary jaw beyond said operating position thereof.

11. A suturing instrument according to claim 1, wherein one of said jaws is provided with a thorn projecting toward the other jaw and the other jaw has a recess receiving said thorn in the operating position of said jaws.

* * * * *